United States Patent
Carrott et al.

(10) Patent No.: US 6,396,940 B1
(45) Date of Patent: May 28, 2002

(54) OPTICAL CORRELATOR BASED AUTOMATED PATHOLOGIC REGION OF INTEREST SELECTOR FOR INTEGRATED 3D ULTRASOUND AND DIGITAL MAMMOGRAPHY

(75) Inventors: David T. Carrott, Palmdale, CA (US); Thomas M. Burke, Bothell, WA (US)

(73) Assignee: Litton Systems, Inc., Agoura Hills, CA (US)

( * ) Notice: Subject to any disclaimer, the term of this patent is extended or adjusted under 35 U.S.C. 154(b) by 0 days.

(21) Appl. No.: 09/322,129

(22) Filed: May 27, 1999

(51) Int. Cl.[7] .................................................. G06K 9/00
(52) U.S. Cl. ...................................... 382/128; 382/132
(58) Field of Search ................................ 382/128, 130, 382/131, 132, 217, 218, 219, 220, 276, 278, 289, 287, 293, 294, 295, 302; 702/155, 159, 171, 172; 128/922; 378/4, 8, 9, 21, 23, 62, 63, 87, 162, 165; 359/306; 348/163; 73/861.08; 708/5, 813, 814, 816

(56) References Cited

U.S. PATENT DOCUMENTS

| | | | |
|---|---|---|---|
| 5,488,674 A | | 1/1996 | Burt et al. .................... 382/284 |
| 5,531,227 A | * | 7/1996 | Schneider .................... 600/425 |
| 5,603,326 A | | 2/1997 | Richter .................... 128/660.07 |
| 5,640,956 A | | 6/1997 | Getzinger et al. ........... 600/427 |
| 5,662,109 A | | 9/1997 | Hutson ..................... 128/653.1 |
| 5,664,573 A | | 9/1997 | Shmulewitz .............. 128/660.9 |
| 5,776,062 A | | 7/1998 | Nields ........................ 600/407 |
| 5,787,889 A | | 8/1998 | Edwards et al. ......... 128/660.07 |
| 5,803,082 A | | 9/1998 | Stapleton et al. ......... 128/653.1 |
| 5,840,022 A | * | 11/1998 | Richter ....................... 600/407 |
| 5,954,650 A | * | 9/1999 | Saito et al. ................. 600/425 |
| 5,983,123 A | * | 11/1999 | Shmulewitz ................ 600/407 |
| 6,102,866 A | * | 8/2000 | Neilds et al. ............... 600/461 |
| 6,208,883 B1 | * | 3/2001 | Holupka et al. ............ 600/407 |
| 6,317,617 B1 | * | 11/2001 | Gilhuijs et al. ............. 600/408 |

OTHER PUBLICATIONS

Burke, Thomas M., "High–Speed Ultrasound Image Improvement Using an Optical Correlator", patent application, 34 pages.

Carson, et al, "Progress In Ultrasonic Computed Tomography (CT) of the Breast", SPIE vol. 173, Application of Optical Instrumentation in Medicine VII, pp 372–381, (1979).

Greenleaf et al, "A Clinical Prototype Ultrasonic Transmission Tomographic Scanner", Acoustical Imaging vol. 12, pp 579–587, (1982).

* cited by examiner

*Primary Examiner*—Andrew W. Johns
*Assistant Examiner*—Shervin Nakhjavan
(74) *Attorney, Agent, or Firm*—Koppel, Jacobs, Patrick and Heybl (57) ABSTRACT

Ultrasonographic information about the internal structure of a subject body is combined with x-ray or other radiographic information from the same subject body by using an optical correlator to quickly find a transformation which aligns the information from both sources, even if they are acquired in different coordinate systems. Various spatial transformations are applied to the information and cross-correlations are quickly performed. The transformation which gives the best cross-correlation is used to align the two data sets, which can then be displayed visually. The resulting display can be used as an aid in medical diagnosis, for example in diagnosing suspected malignant lesions in a woman's breast.

22 Claims, 7 Drawing Sheets

OPTICAL CORRELATOR BASED AUTOMATED PATHOLOGIC REGION OF INTEREST SELECTOR FOR INTEGRATED 3D ULTRASOUND AND DIGITAL MAMMOGRAPHY

BACKGROUND OF THE INVENTION

1. Field of the Invention

The invention relates generally to ultrasonic and radiographic non-invasive methods for examining tissue or other solids. In particular, the invention relates to the coordination or fusion of ultrasonic sonograms with x-ray or other radiographic imaging techniques, to aid in the detection of areas of interest, such as lesions in a human breast.

2. Description of the Related Art

Various means of non-invasive imaging are useful in medicine and other fields for visually modeling the interior structure of a solid subject body. For example, a very common method of screening women for breast cancer is x-ray mammography. Ultrasonic imaging is another, less common technique for examining breast tissue.

X-ray mammography provides excellent detection of certain types of tissues, but nevertheless has shortcomings. This technique provides detailed image information about dense materials within the body (such as bone or other calcified tissue), but it performs poorly at discriminating between soft tissues with subtle differences in density and structure. Some women have mammographically dense breasts (compared to more fatty breast tissue); there is a substantially increased risk of missing breast cancers when diagnosing such women by x-ray. The use of x-rays for examination also necessarily results in the exposure of the patient to ionizing radiation, which has well know associated risks. The technique is also limited in that it projects three-dimensional structure onto a two-dimensional plane, and thus does not capture the elevation or depth (position in the direction of radiation propagation) of features of interest.

A newer imaging technique, ultrasonic imaging, is widely used for diagnosis in numerous medical fields. When properly used and adjusted, an ultrasound imaging system can non-invasively provide a cross-sectional view of soft tissue being imaged, such as the tissue of a breast, heart, kidney, liver, lung, eye, abdomen, or pregnant uterus.

A typical ultrasound imaging device operates by directing short ultrasonic pulses, typically having a frequency in the range of 1–30 MHZ, into the tissue being examined. The device then detects responses such as echoes, harmonics, phase or frequency shifts, of the ultrasonic pulses caused by acoustic impedance discontinuities or reflecting surfaces within the tissue.

A typical scanhead for an ultrasonic imaging system has a linear array of ultrasonic transducers which transmit ultrasonic pulses and detect returned responses. The array of transducers provides simultaneous views of the tissue at positions roughly corresponding to the positions of the transducers. The delay time between transmitting a pulse and receiving a response is indicative of the depth of the discontinuity or surface which caused the response. The magnitude of the response is plotted against the position and depth (or time) information to produce a cross-sectional view of the tissue in a plane perpendicular to the face of the scanhead.

Sophisticated ultrasonic imaging systems are available which are capable of assembling information from multiple two-dimensional cross-sections to form a three dimensional representation of subject tissue. Such systems are potentially useful in the diagnosis of suspicious lesions in the breast. Compared to x-ray techniques, the ultrasonic imaging is advantageous in that the patient is not exposed to radiation. Ultrasound is also superior for imaging many types of soft, low-density "hidden masses" which are typically invisible or very obscure in x-ray imagery. On the other hand, the lower resolution of ultrasonic imaging (compared to x-ray) makes it incapable of identifying fine features, such as hard micro calcifications in breast tissue, which would be visible in an x-ray.

Although a patient (or other subject body) can be subjected to multiple imaging techniques (for example x-ray and ultrasound), the images obtained are not easily registered or correlated with one another. Differences in scale, position, or in the orientation of the plane of projection (of a two-dimensional image) are almost inevitable.

U.S. Pat. No. 5,531,227 to Schneider (1996) discloses a method and apparatus for obtaining an image of an object obtained by one modality such that the image corresponds to a line of view established by another modality. However, the method disclosed requires one or more fiducial markers to inter-reference the images. The preferred method disclosed also involves mounting the patient's head immovably to a holder such as a stereo tactic frame, which is inconvenient for the patient and the technicians. The method identifies fiducial markers by digital segmentation, feature extraction, and classification steps, which would most suitably be performed with powerful digital hardware and custom software. The method disclosed will perform best with fiducial markers which are easily automatically recognized, as by some simple geometric property; it is described in connection with using circular eye orbits as fiducial markers. In some human tissues, however, such natural geometric features may not be readily available.

Another method of correlating ultrasonic image data with radiographic image data is disclosed in U.S. Pat. No. 5,640, 956 to Getzinger et al (1997). This method requires that an x-ray image be obtained while the tissue is in the same position as it was while the ultrasonic data was being gathered. It also requires the use of fiducial reference markers (preferably multiple x-ray opaque reference markers).

SUMMARY OF THE INVENTION

The invention is an apparatus and method for quickly coordinating ultrasonographic information about the internal structure of a solid subject body with x-ray or other radiographic information taken from the same subject body.

Given a radiographic transmission image of a subject body, and given further a set of three dimensional image data composed of tomographic slices of the same subject body, the invention relates a region in the original radiographic image to a region within the three-dimensional image data by using two-dimensional image cross-correlation, preferably performed by an optical correlator. In the preferred embodiment, the invention also uses a two-dimensional cross-correlation to find the elevation of a feature of interest in the three-dimensional data set.

Provided that the differently obtained images include at least some overlap, it is not required that the ultrasonographic and the radiographic images share identical or previously related scales, positional axes or spatial orientation. They may be taken from different angles, at different scales, or with the subject positioned and rotated differently in each image. The invention determines and applies the translations, rotations and scale transformations required to best correlate the radiographic information with the ultrasonographic information corresponding to the same physical region and view of the subject body.

BRIEF DESCRIPTION OF THE DRAWINGS

FIG. 4b is a flow chart continuing from FIG. 4a, joining FIG. 4a at cut line A and FIG. 4c at cut line B, showing the continuation of the procedure of FIG. 4a;

DETAILED DESCRIPTION OF THE INVENTION

Figure 1:
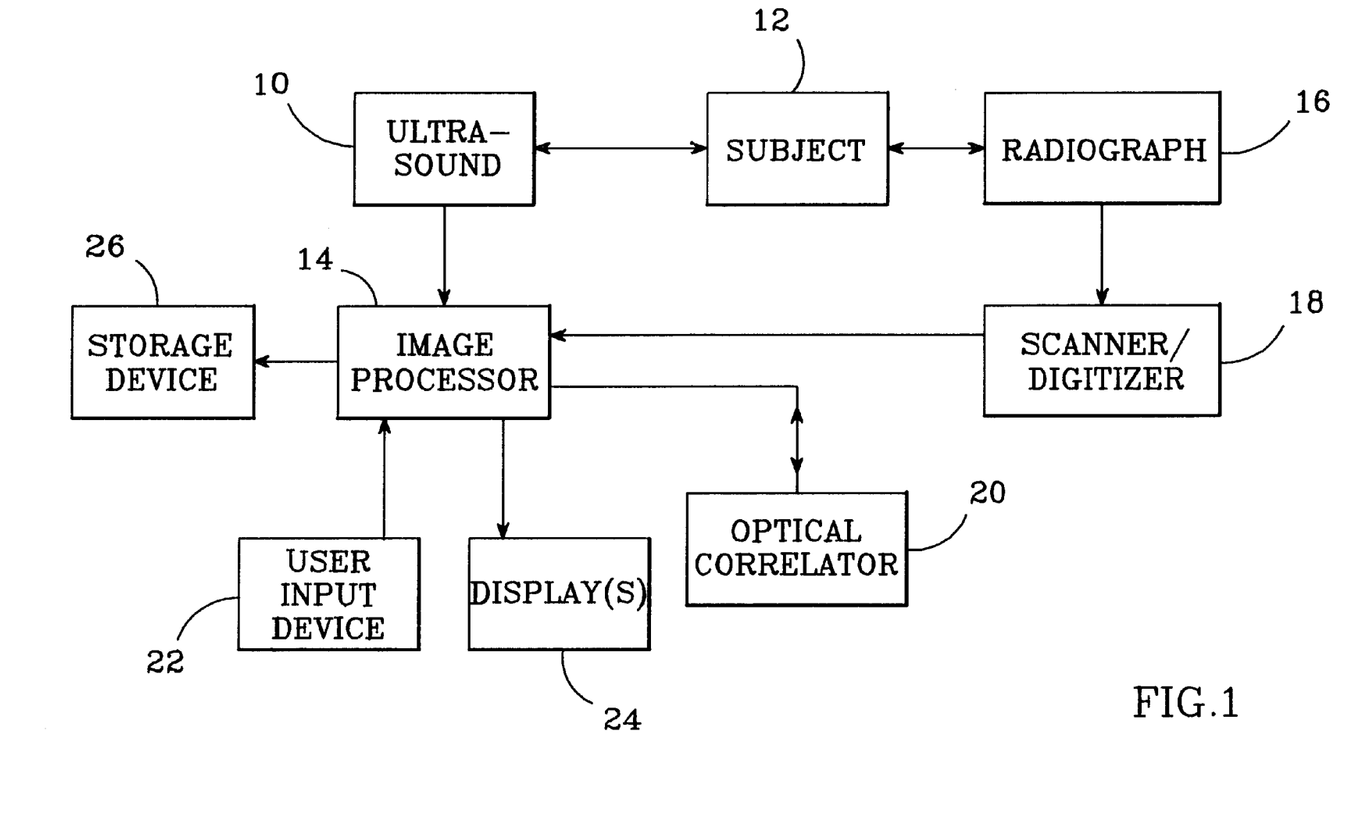
FIG. 1 is a system level block diagram of the invention.

In FIG. 1 a conventional ultrasound imaging system 10 scans a subject body 12 (for example, a human breast) to obtain three-dimensional ultrasonographic imagery revealing the composition of the subject body, by analysis of echos returned from internal structures of the subject body. This ultrasonographic imagery is provided in digital form to an image processor 14 for further analysis, processing and storage. An x-ray or other radiographic device 16 examines the same subject body (breast), in general from an angle which may be different from the angle used by the ultrasonographic imaging system 10. The position and rotation of the breast can and generally will differ from that used during the ultrasonography as well. The radiographic examination may be done at approximately the same time as the ultrasonography, but this is not essential. The x-ray or other radiographic imagery is digitized (either directly from detectors or indirectly using a digital image scanner/digitizer 18 on a conventional x-ray photograph). Image processor 14 processes and stores the digitized radiographic imagery, preferably in an x-ray image database. The image processor 14 then controls an optical correlator 20 to analyze correlations between the processed and stored radiographic and sonographic imagery.

The image processor 14, which could be either a specialized processor or a general purpose computer, is programmed to apply various coordinate transformation to the radiographic and/or the ultrasonographic imagery. For example, the image processor 14 may apply various multi-plications of scales, rotations, and translations. The resulting processed imagery, ultrasonographic and radiographic, is then output to the optical correlator 20, which returns a correlator output image to the image processor 14. By exploiting the high speed and image processing capabilities of presently available optical correlators, the image processor 14 is able to quickly perform numerous test correlations on variously transformed ultrasonographic and radiographic images, producing numerous correlator output images from optical correlator 20, with varying degrees of correlation. Although the ultrasonographic and radiographic images are not identical, common features visible in both images will produce a maximum degree of correlation when the images are aligned with one another and oriented in the same manner. The image processor 14 selects the transformations which produce the optimal output correlation, then applies these transformations to at least one of the radiographic and ultrasonographic images, thereby properly aligning the images.

In the preferred embodiment of the invention, the image processor 14 further correlates the transformed (properly scaled, translated, and rotated) radiographic information with data subsets (planes or surfaces) of the three-dimensional ultrasonographic information to provide a sophisticated diagnostic imagery which integrates both sources of information and reveals the variation in the degree of correlation from one plane to another. The original and the correlated images, as selected by a user via input device 22, are displayed on display(s) 24 (for example, a video monitor and/or a printer) for viewing. The combined data may also be output from image processor 14 to a storage device 26 which stores the information and transformation parameters on a computer readable medium.

The invention thus coordinates the two independent sets of imaging data, thereby providing more complete imagery for analysis (typically by a physician). The ultrasound imagery provides superior soft tissue information, while the radiographic imagery provides superior information on calcified or hard masses; the invention coordinates the two information sets and, in the preferred embodiment, creates a correlated or fused three-dimensional data representation of the subject body for display and analysis.

Figure 2:
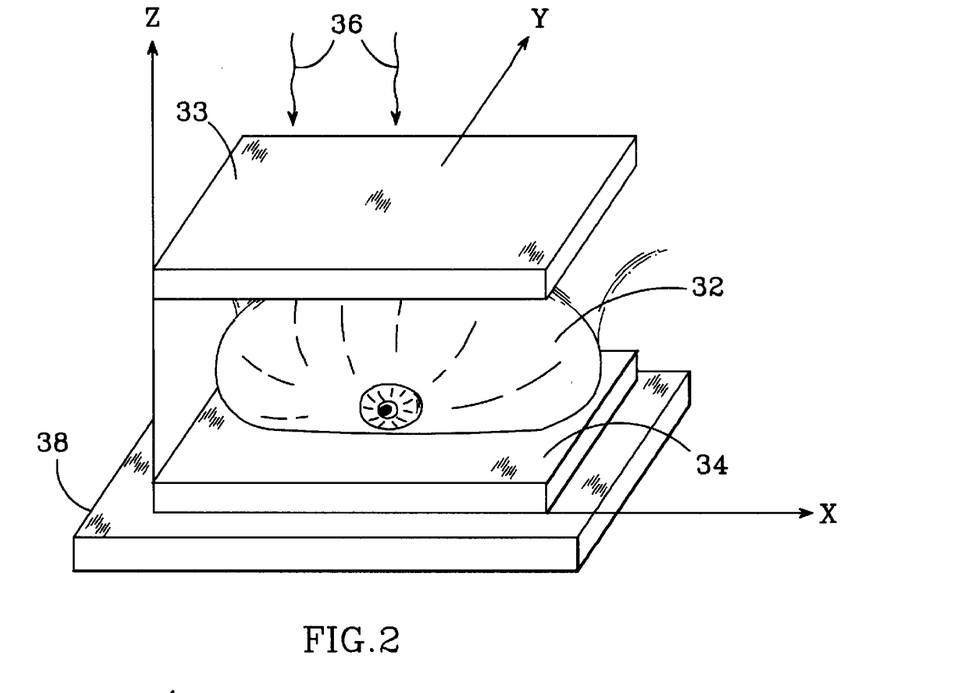
FIG. 2 is a perspective view of one arrangement for obtaining x-ray images for use by the invention.

The detailed operation of the invention and its various subsystems are best described with reference to an example of a particular coordinate system, to aid in visualization. FIG. 2 shows how the sonographic and radiographic images or information might be obtained from a human breast presented for diagnosis, a typical application of the invention (although the techniques are not limited to use in medicine). The system is conveniently illustrated in a Cartesian, rectilinear coordinate system having linear, perpendicular axes x, y and z, but the invention is not limited to such a coordinate system.

Assume a human breast 32 is positioned between an upper and lower pressure plates 33 and 34, as shown in FIG. 2. An x-ray or other radiographic image is formed in the conventional way by illuminating the breast with radiation 36 propagating downwards in the figure, with rays parallel to the z axis (toward −z). By exposing an x-ray sensitive plate 38 in the conventional manner an image is formed which indicates the projection of the breast's radiation absorption onto the plate 38 which lies in the x-y plane. Alternatively, a radiation detector or detectors in the x-y plane can be used to provide a two-dimensional array of absorption values by scanning the absorption at each point in the plane. Either method results in an image: a projection of the internal structures of the breast onto a plane. The image is scanned and digitized by scanner/digitizer 18 for storage and processing by image processor 14.

Mammographic equipment is commercially available from a variety of commercial sources which will perform the above described functions substantially in the manner described.

Figure 3:
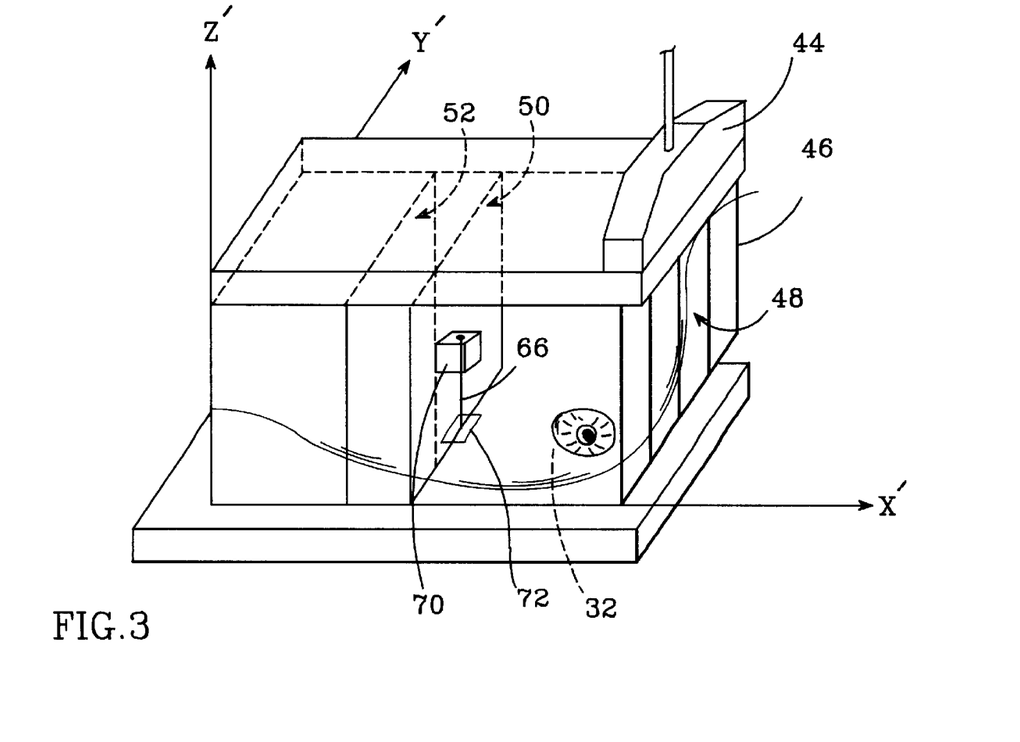
FIG. 3 is a perspective view of one geometric setup which can be used to obtain ultrasonographic imagery for use by the invention.

Either before, after, or simultaneously with the radiography, the same breast 32 is scanned with ultrasound by the ultrasonic imaging system 10, preferably as shown in FIG. 3. With a patient preferably sitting facing the imaging system, the patient's breast 32 is preferably slightly compressed between upper and lower pressure plates 33 and 34 as in the x-ray setup. To produce the most consistent results, the breast should preferably be under the identical pressure (between pressure plates 33 and 34) as was used in the previous radiographic technique. In positioning the breast between the pressure plates, edges of the plates will contact the patient's chest above and below the breast. Because of inconsistencies in positioning the patient's breast in the imaging system, the x', y' and z' axes of FIG. 3 do not in the general case exactly correspond with the x, y and z axes of FIG. 2, but may differ by a coordinate transformation: for example, they may differ by translation in the x or y directions, and by rotation about any axis. Rotation about the z axis is especially likely.

With the breast 32 in position, conventional ultrasonic scanning is preferably performed in planes (or surfaces), which will in general be non-parallel to that of the radiographic image (x-y plane in FIG. 2). FIG. 3 shows a typical geometry in which the scanhead 44 includes a linear array of ultrasonic transducers aligned parallel to the y' axis. The scanhead 44 transmits ultrasonic pulses in the directions of the parallel lines 46, which are preferably perpendicular to the x'-y' plane and parallel to the z'-y' plane. The array of transducers in scanhead 44 probe the underlying tissue lying (approximately) on lines 46 by detecting returns of the ultrasonic pulses caused by acoustic impedance discontinuities or reflecting surfaces within the tissue. The delay time between transmitting a pulse and receiving an return is indicative of the depth of the discontinuity or surface which caused the return. A characteristic such as magnitude, phase, or frequency of the returns is digitized and is plotted against the depth (z' axis) information and the information from the multiple transducers (dispersed in the y' direction) is assembled to construct an array representing a cross-sectional view of the tissue in a slice 48 parallel to the y'-z' plane and lying under scanhead 44.

Multiple slices can be scanned either by providing multiple scanheads, a two-dimensional scanhead array, or by moving the scanhead across the breast, for example in the y direction in FIG. 3. Only a few of the multiple slices, specifically slices 48, 50, and 52, are shown. In practice a large number of slices is desirable, for better resolution. A complete set of such slices is preferably scanned to form a three dimensional information set for at least some region of interest (ROI) chosen from the breast, which is preferably stored in a data structure (such as a three-dimensional array) to represent a three-dimensional image.

Ultrasonographic equipment is available commercially which can be used as the ultrasonographic imaging system 10 described above. Three-dimensional information is desirable but not necessary to the invention. A two-dimensional array of ultrasonographic data can be correlated by the invention, but with a diminished amount of useful information in the resulting display, as described below.

Once the ultrasonographic image has been scanned by ultrasonographic imaging system 10, the image processor 14 uses the optical correlator 20 to determine the most correct scalings, rotations and translations of the two-dimensional radiographic information to properly relate it to the ultrasound image derived from the same breast. This is necessary because the breast may not be (and in general will not be) oriented in precisely the same position during the acquisition of the ultrasound information as during the x-ray or radiographic exposure. The scale of the radiographic image relative to the ultrasonographic images may also vary slightly, in spite of any attempts at cross-calibrating the radiographic and the ultrasonographic equipment.

Figure 4A:
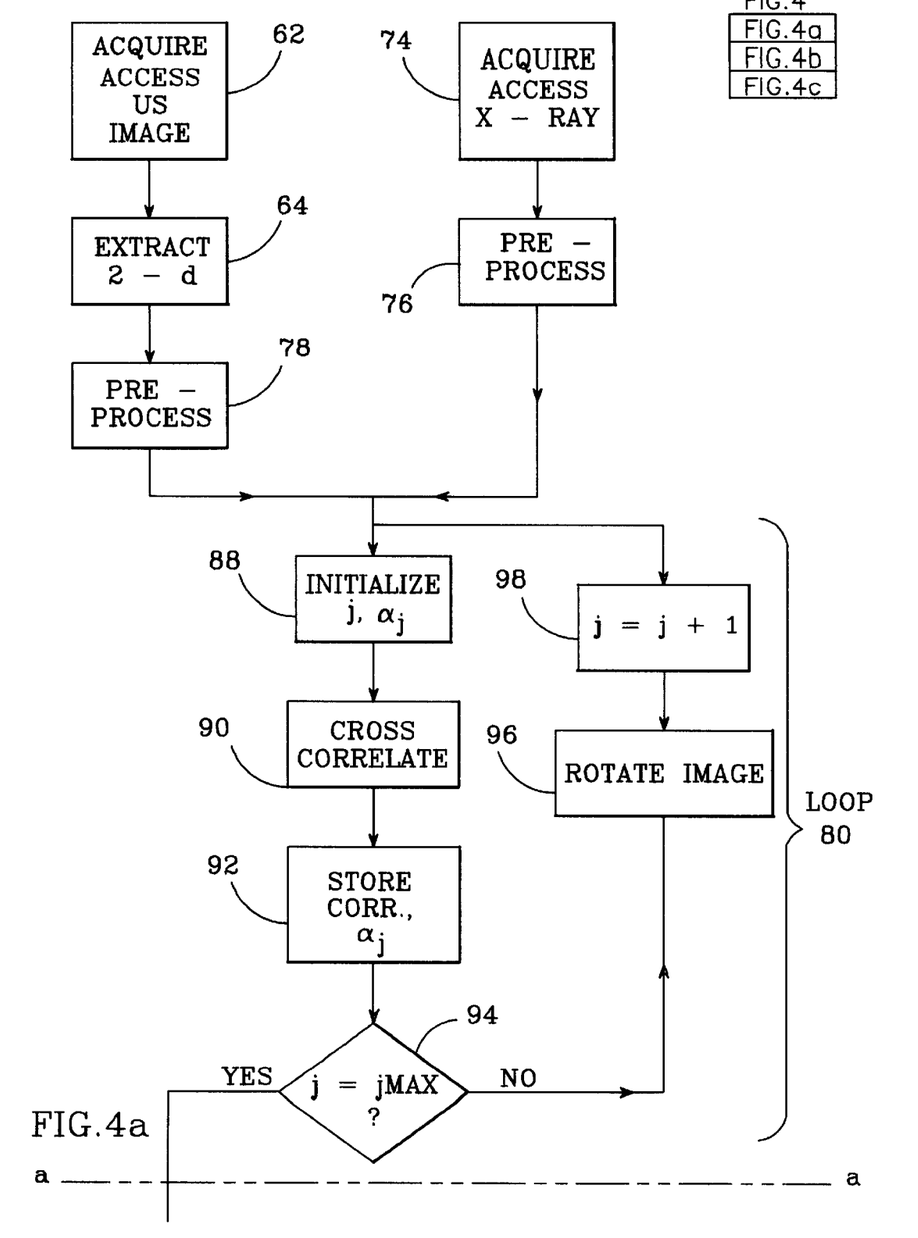
FIG. 4a is a flow chart reading top-to-bottom and joining FIG. 4b at cut line A, showing initial steps of a procedure preferably used to find an optimal transformation to correlate the ultrasonographic and radiographic images.

FIG. 4a shows the preferred procedure by which the image processor determines the proper coordinate transformations of scale, position, and rotation which will coordinate the ultrasound data with the radiographic data. The image processor 14 accesses (step 62) the stored ultrasound data from ultrasonographic imaging system 10 and extracts (step 64) a two-dimensional representation by projecting or "collapsing" the three-dimensional ultrasound data onto a single plane. One method of doing this is by "cumulative projection": a projection of the three-dimensional data set onto a two-dimensional plane by summing the data entries along vectors which are perpendicular to the projection plane. One such vector, vector 66, is indicated on FIG. 3 for illustration. The density values associated with the voxels (three dimensional discrete volume cells) such as voxel 70 are summed along the vector 66. The summation of those density values yields a scalar value which indicates the sum of the tissue densities along that vector. This scalar value is associated with the pixel 72 at the intersection of the vector 66 with the x'-y' plane. Repeating this summation for multiple parallel vectors results in a set of values which defines the projection of the three-dimensional sonographic imagery onto the x'-y' plane.

Referring again to FIG. 4a, either before, after or during extracting the two-dimensional ultrasonic data (for example, by the previously described method), the image processor 14 accesses (step 74) the two-dimensional x-ray information from an x-ray database and preferably pre-processes (step 76) the x-ray imagery. The x-ray pre-processing 76 can include any of a variety of known image processing techniques including (without limitation) contrast modification, smoothing, geometric transformation, thresholding or the selection of a region of interest. Depending on the type of optical correlator 20 used, as discussed in detail below, this step may also include two-dimensional Fourier transformation of the digitized x-ray image to prepare it for subsequent optical correlation in a Vanderlugt optical correlator. Preprocessing may also (optionally) be applied (step 78) to the ultrasound image data.

Next the image processor 14 adjusts the relative scale of the two images so that they at least approximately correspond in scale. This can be done by various methods. For example, one method is to match the total area of the cross section of the breast area between the outer outline and the chest wall in both images. In this method, the images should preferably first be processed to remove low contrast features, leaving only the easily visible outline of the breast and the chest wall. The area between these features in the two dimensional images is then measured, for example by numerical integration by the image processor 14. The area should correspond in both images, after taking into account known peculiarities of the imaging methods. For example, certain ultrasonographic breast imaging systems fail to image the outer 10 to 20 per cent of the breast. If the two areas do not correspond (after correcting for peculiarities), a scaling factor, equal to the ratio of the areas, is calculated and applied to equalize the scales.

It is possible in many cases to maintain a previously known relative scale between the ultrasound and the x-ray apparatus. In such cases, little or no re-scaling is necessary.

Another simple method of determining relative scale is by placing a fiducial marker or markers in both the x-ray and the ultrasonographic image. For example, distinctive metallic foil or wire markers can be placed a known distance apart, under the breast while both images are acquired. Alternatively, a single marker of known size could be used. The resulting distinctive mark or marks can be recognized in the acquired images, either by visual inspection or by processing by image processor 14, to compare the imaged markers. It is then simple to find the scaling factor by dividing the apparent separation (or size) of the markers in one image by their apparent separation (or size) in the other image. The image processor then saves the scale factor and uses it to transform the images to a common scale. It is not necessary to maintain the position of the marker(s) with respect to the breast to recover the proper scale factor.

Once the radiographic and ultrasonographic images have been transformed to a common scale, the image processor 14 determines the rotation and translation necessary to align the images, preferably by interactively performing the steps grouped within the instruction loop 80 in FIG. 4a. First, two variables are initialized (step 88): a counter j to control execution of an instruction loop, and an associated rotation angle $\alpha_j$. Next, a cross-correlation of the dual images is computed (step 90). Preferably this step is accomplished by using an optical correlator 20 to perform the actual correlation computation, under control of the image processor 14. (The details of the optical correlator are discussed below, in connection with FIGS. 5 and 6) The cross-correlation (step 90) produces a two-dimensional correlation output image indicating the degree of cross-correlation, which is stored (step 92) along with the associated rotation angle $\alpha_j$. The image processor then checks (step 94) the counter variable to discover whether it has completed a prescribed number of iterations of the instruction loop 80.

Next, if the counter variable j has not reached jmax, the image processor 14 continues and rotates (step 96) one of the dual images relative to the other by some angular increment, for example by rotating the x-ray image one degree about an axis centered in the x-ray frame and parallel to the z axis. The counter is incremented (step 98) and the procedure loops back to step 90 to perform another cross-correlation, this time with the images rotated incrementally. The procedure is repeated until some number (jmax) of differently rotated correlations has been performed. The parameter jmax should be chosen to be large enough so that the range of the associated angle $\alpha_j$ encompasses the anticipated maximum possible range of rotation. For breast examination in the geometry shown in FIG. 3, a range of 45 degrees is adequate.

The rotations applied in step 96 are not limited to rotations about a single axis, but could include rotations about multiple independent axes (or, equivalently rotations about an axis obliquely oriented with respect to the orthogonal axes shown). This allows the correction for an oblique viewing angle of one image with respect to the viewing angle of the other.

After the counter j reaches jmax the image processor 14 exits the instruction loop 80. The procedure continues as diagramed in FIG. 4b. The correlation output images previously stored in the various iterations of step 92 are compared (step 100) with one another to find the correlation output image with the maximum correlation, and its associated angle of rotation $\alpha_j$. The value $\alpha_m$ (the rotation angle which produced maximum correlation) is stored (step 102) and either the ultrasonographic imagery or the radiographic image is rotated (step 104) by $\alpha_m$ to bring it into the same orientation as its counterpart. Preferably the radiographic image is rotated to align with the (three-dimensional) ultrasonographic imagery, because rotating the typically larger database associated with the three-dimensional ultrasonographic imagery would require more computations than are required to rotate the two-dimensional radiographic database.

Figure 5A:
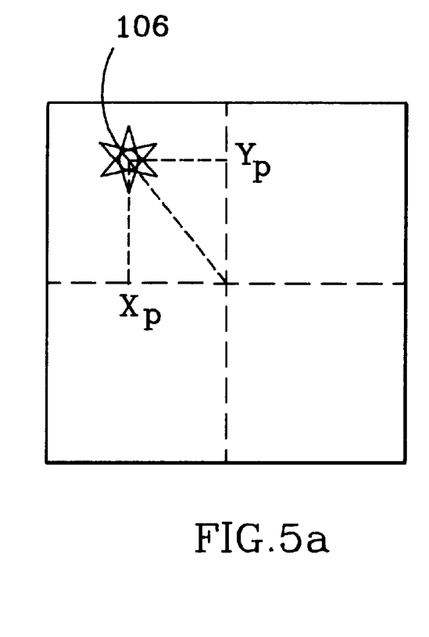
FIGS. 5a, 5b, and 5c, show simplified examples of an input image, a filter template, and a resulting correlation output image, respectively, in an example of a cross-correlation operation which discovers positional offset of correlated images.
Figure 5B:
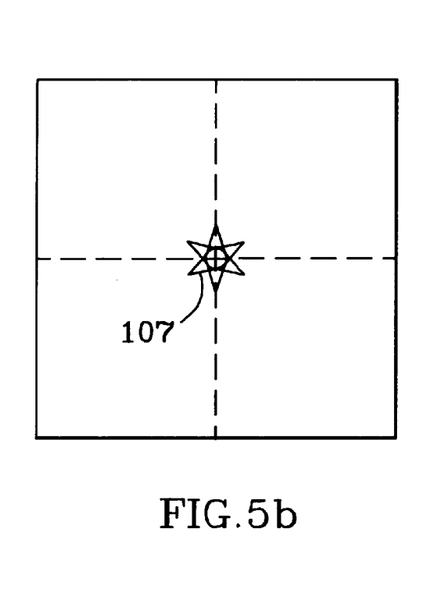
Figure 5C:
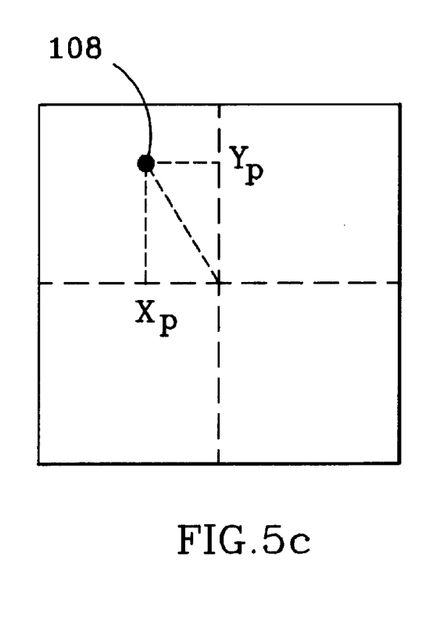

It should be understood that in addition to discovering the correct scale and rotation angles, the cross-correlation (step 90) in the above described procedure produces an output image which reveals the correct translation (position shift) which best aligns the dual images. The translation information is contained in the result of the cross-correlation operation (preferably in two-dimensions) defined as:

$$H(x,y)=g(x,y)*f(x,y)=\int\int f(\alpha,\beta)g(x-\alpha,y-\beta)d\alpha d\beta \qquad (1)$$

Where f and g are functions of two variables (images), x and y are the spatial variables of the two-dimensional images, $\alpha$, and $\beta$ are dummy variables of integration, H is the cross-correlation of functions f and g, and the range of integration is across the entire image. If f and g differ only by a positional offset in x and y, H(x,y) will have a sharp peak at a position $x_p,y_p$ which is displaced from a central, correlation alignment position (typically defined as x=0, y=0) by a displacement corresponding to the offset between f and g. This well known result has been used to recognize and locate features of initially unknown locations in a field by reference to a template. See, for example, Russ, John C., *The Image Processing Handbook* (CRC Press, 1992), pp. 218–24. A simplified example is shown in FIGS. 5a–5c. The input image, a star 106 at an offset position shown in FIG. 5a, is correlated with a filter derived from the centered star-shaped template 107 shown in FIG. 5b. The resulting correlation output shown in FIG. 5c has a peak 108 at a position $x_p,y_p$ corresponding to the offset between the input image and the filter template. To align the images with a correlation peak at position $x_p,y_p$ it is sufficient merely to translate one of the images by a displacement equal to the offset $x_p,y_p$.

If the subject breast 32 is differently oriented in the x-ray and the ultrasonographic image, it will most likely be rotated slightly about a vertical axis (parallel to z axis) which lies somewhere within the patient's body. This is equivalent to a translation plus a rotation of the image frame about its center, both of which are discovered and corrected by the procedure of FIGS. 4a through 4c.

Returning to FIG. 4b, the image processor 14 next analyzes (step 114) the correlation output image to locate the positional offset of the correlation peak from an aligned correlation position, then translates (step 116) one image relative to the other as necessary to better align the images. After finding the optimal combination of rotations, scalings and translations which properly align the radiographic with the ultrasonographic information, the image processor 14 preferably stores (step 118) the transformed images and the transformation parameters in its associated memory and preferably outputs (step 120) the transformed images to a display device 24. The visual output can be displayed in various forms, and should preferably be structured to make apparent the spatial relationship between the x-ray and the ultrasonographic images. Various display formats can be used to allow the simultaneous display of both data sets in proper relation to the common coordinate system discovered by the invention. For example, overlays, color coding, projection onto various planes, topographic quasi-three-dimensional display formats could be used, in various combinations. The transformed images and the transformation parameters are also preferably stored by storage device 26 on a computer readable medium.

Figure 6:
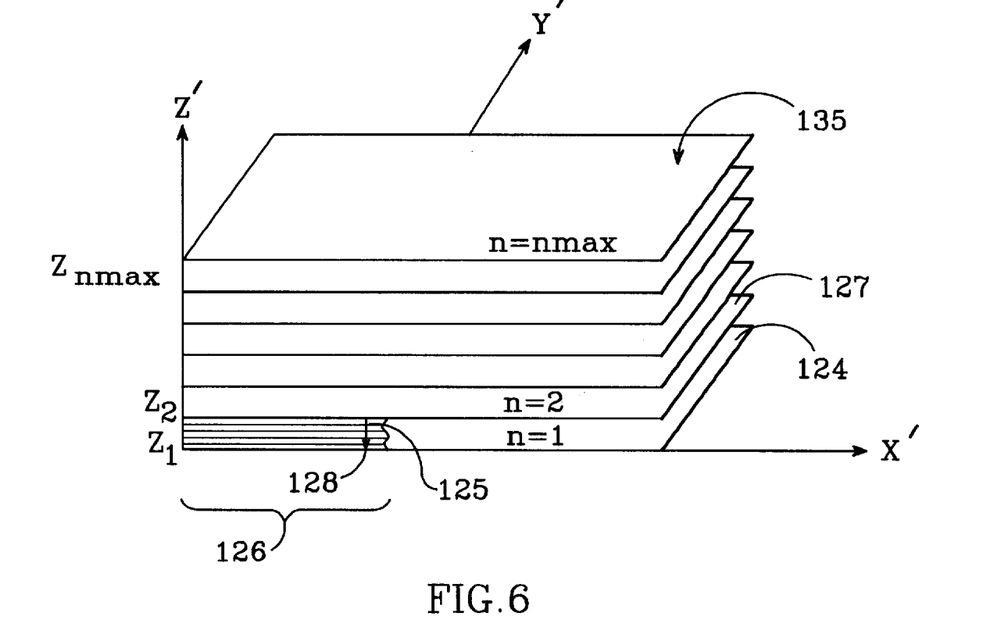
FIG. 6 is a perspective view of an arrangement of planar slices of a subject body which can be selected for analyzing a subject body by the invention.

In one embodiment the invention provides additional three-dimensional information about the subject body by further correlating the ultrasonographic and the radiographic images in order to locate the depth (z coordinate) of such features. To locate the depth of features of interest, the ultrasonographic imagery is first partitioned by image processor 14 into conveniently defined slices, for example slice 124 as shown in FIG. 6. Each slice includes one or more layers of the three dimensional ultrasonographic image data. The slices are defined and calculated by image processor 14, for example by summing data points along vertical vectors such as 125, to collapse multiple thin layers into a thicker slice (a "partial cumulative projection"). In FIG. 6, for example, three thin layers 126 of ultrasonographic imagery (shown only partially to clarify FIG. 6) might lie between bottom slice 124 and the immediately overlying slice 127. The partial cumulative projection is taken point-by-point, by summing the ultrasonographic image values at points along vectors such as vector 125, and accumulating the result to the point 128 where vector 125 intersects the slice 124. The accumulated data values at each defined point on slice 124 collectively define the slice.

In a typical application, slices of 5 millimeters in thickness are suitable. Although planar slices are convenient for purposes of illustration, in some applications the slices might usefully be taken along non-planar contours. Such slices are also within the scope of the invention. Thinner slices are desirable for better depth definition with thin features, but may result in poor correlation if the feature of interest is distributed in depth by more than the defined slice thickness. The x', y',z' axes of FIG. 6 are not, in general, identical to the x,y,z axes of FIG. 2; rather, they may be rotated (about any axis) and translated (by an x,y,z vector) with respect to the x,y,z axes.

Figure 4B:
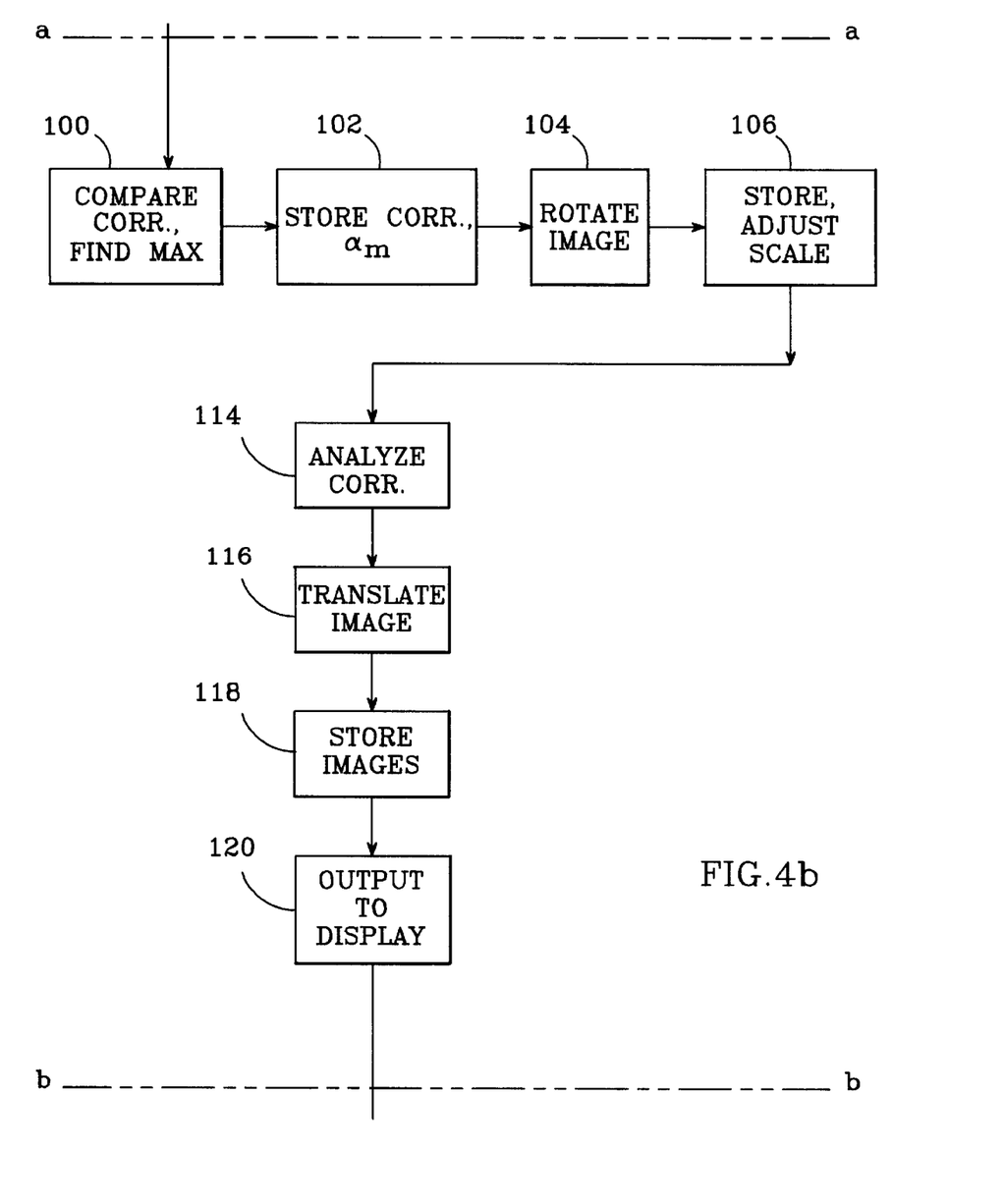
Figure 4C:
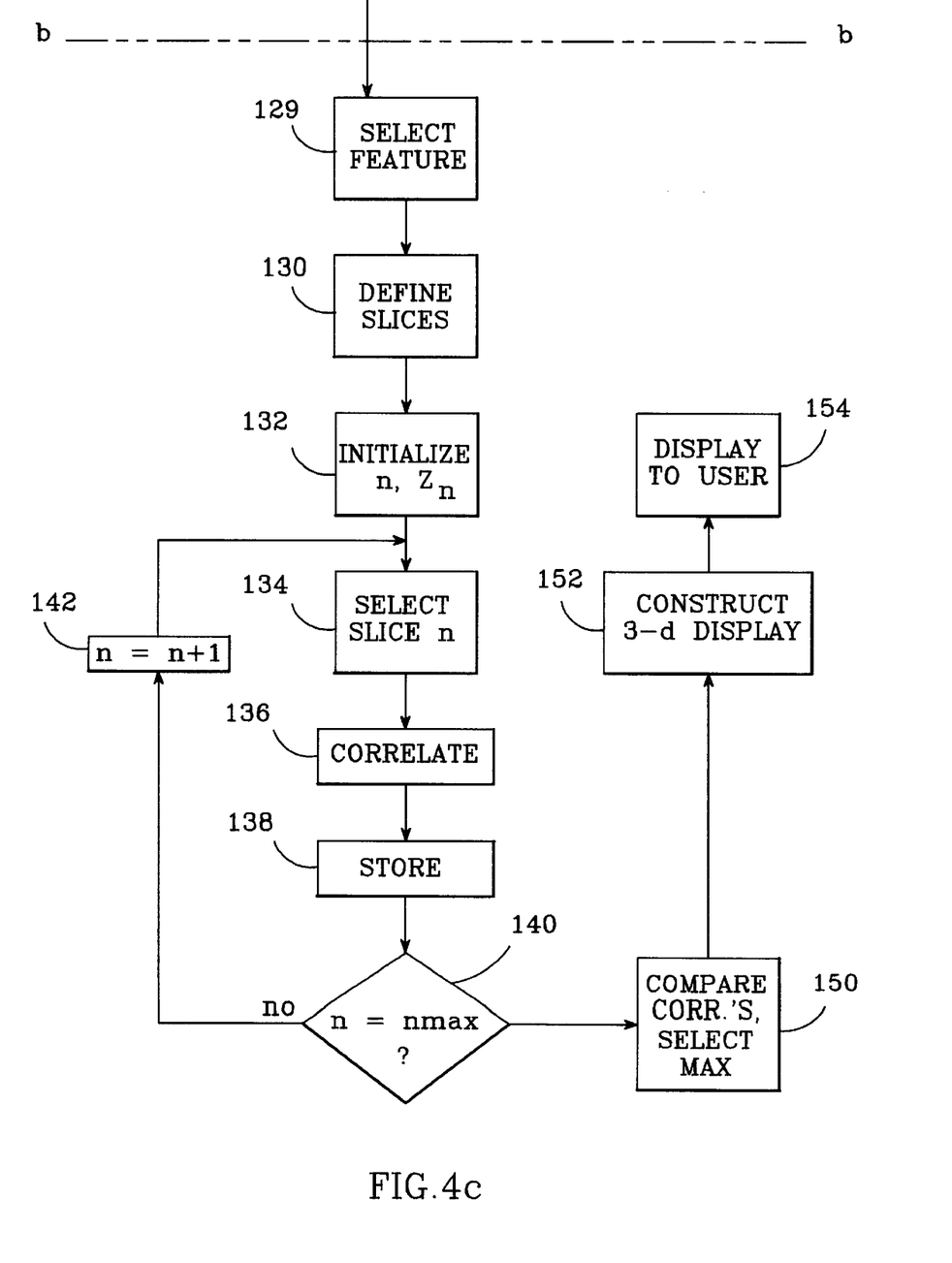
FIG. 4c is a flow chart continuing from FIG. 4b and joining FIG. 4b at cut line B, showing the procedure used by one embodiment of the invention to further relate the ultrasonographic and radiographic images in three dimensions.

FIG. 4c shows one procedure which is suitably used (preferably subsequent to the procedure of FIGS. 4a and 4b) in an embodiment of the invention which locates the depth of solid features of interest. Such features are preferably user selected (step 129) by input to the image processor 14 from a user input device 22. In this embodiment, having previously determined and applied the proper scale, rotation and translations to align the x-ray information and stored the transformed images, the image processor 14 defines slices (step 130) as discussed above in connection with FIG. 6. The image processor 14 then initializes (step 132) a counter variable n. This variable is used to index multiple parallel planar slices which intersect the z' axis at different positions.

The image processor 14 then selects (step 134) a planar slice at depth $Z_n$ from the three dimensional ultrasound data, for example slice 125 which is parallel to the underlying transformed x-ray image plane (the x'-y' plane in FIG. 6). The extracted slice is then correlated (step 136) with the transformed x-ray image or with a user selected ROI taken from the x-ray image. The image processor 14 controls correlation of the slice (which is preferably performed by the optical correlator 20), stores (step 138) the correlation array and its associated depth $Z_n$ in memory, checks (step 140) the counter to find out whether the counter has reached maximum n, and if not, increments (step 142) a counter, then loops back to select another slice at a different depth for correlation (step 134).

After a programmed number (maximum n) of slices have been selected and processed, the counter n reaches maximum value nmax, corresponding to the uppermost plane 135 in FIG. 6. The plane with the maximum correlation for the feature of interest and its associated depth $Z_n$ are stored in memory (step 150). One or multiple features of interest may be selected and correlated, and the resulting plane(s) of maximum correlation used to construct (step 152) a multi-planar, three-dimensional data structure identifying the three-dimensional locations of the features of interest.

The three-dimensional imagery constructed by the procedure of FIG. 4c is preferably then displayed visually (step 154) to a user by the display 24. As described above, various means of symbolic representation or three-dimensional projection graphics can be used to present the information effectively. The three-dimensional construction is also preferably stored by storage device 26 in a computer readable medium.

By determining the depths of features of interest, the invention can be used to compose or construct a composite, three dimensional representation of the subject body, incorporating information from both ultrasound and x-ray imagery. Thin features (with low thickness in the z direction) will result in a particularly good correlation which is well restricted to the slice at the actual depth of the feature, with poor correlation in other slices.

Combining the ultrasound and the x-ray images by the invention is in itself useful for displaying or analyzing internal structures of a solid body. In addition the invention offers specific advantages in analyzing or diagnosing biological tissues. For example, to diagnose human breast cancer it is helpful to detect and locate prognostic indicators (tell-tale signs of cancer which lie at or near the cancerous lesion). Some prognostic indicators, such as hard microcalcifications, are most easily seen in x-ray images. Others, such as a density of atypical lobules, are much more easily seen in ultrasound derived images. By combining the two images into a single data structure which properly relates the x-ray and ultrasound images in space, a physician can visually determine whether two such prognostic indicators are occurring at the same location in the breast. Since the randomly caused coincidence of two such statistical indicators is improbable (provided that the two indicators are truly independent), the spatial coincidence of two independent in-situ could provide a stronger indication of a malignant lesion than either independent observation would provide. By coordinating the x-ray and the ultrasound imagery, the invention thus provides a new diagnostic tool.

In the procedures depicted in FIGS. 4a, 4b and 4c, it is highly preferable that the correlation operations be carried out by an optical correlator. In the preferred embodiment, the image processor 14 electronically writes the dual images to the optical correlator 20. The optical correlator 20 preferably performs the correlation operations and returns a resulting correlation image to the image processor 14.

Optical correlators use wave optics to correlate images in two dimensions by first performing essentially a two-dimensional spatial Fourier transform on a two-dimensional source image. This method takes advantage of a well known mathematical property of the Fourier transform: many operations including correlation are more easily calculated in the Fourier transform domain than in the original spatial domain. Specifically, a two-dimensional correlation operation is defined by equation 1 (above), where f(x,y) and g(x,y) are the two-dimensional functions or images to be cross-correlated, and $\alpha$ and $\beta$ are dummy variables of integration. This operation can be performed digitally for each point x,y by numerical techniques, but a very large number of calculations are required even for one image correlation. Performing such an operation digitally is very time consuming and requires inconvenient lengths of time on any but the fastest digital computers.

Unlike a conventional digital computer, an optical correlator can very rapidly perform a correlation operation, correlating a source image with a filter image by (1) optically Fourier transforming a source image, (2) comparing the source and filter image in the Fourier transform domain, and then (3) performing an inverse Fourier transformation to produce the correlation pattern in a spatial representation. An optical correlator can accomplish these operations much faster that a digital computer because the optical Fourier transformation is executed as a simultaneous operation on all points of the source image, using inherent properties of wave optics to generate the Fourier transform in two dimensions. The speed of the device is limited for practical purposes only by the available read and write speed of the data transfer to the correlator; the actual optical processes occur in fractions of a nanosecond in typical optical correlators.

The principles of the optical correlator are known, and have been described for example in the U.S. Pat. No. 5,311,359, to Lucas et al. Compact optical correlators suitable for use in the present invention are commercially available from Litton Data Systems, Inc., in Agoura Hills, Calif., as well as from other sources. Alternate types of optical correlators such as the Joint Transform Correlators described in U.S. Pat. No. 5,650,855 to Kirsch et al., U.S. Pat. No. 5,216,541 to Taksue et al. or U.S. Pat. No. 5,438,632 to Horner, may also be employed with the invention.

Figure 7:
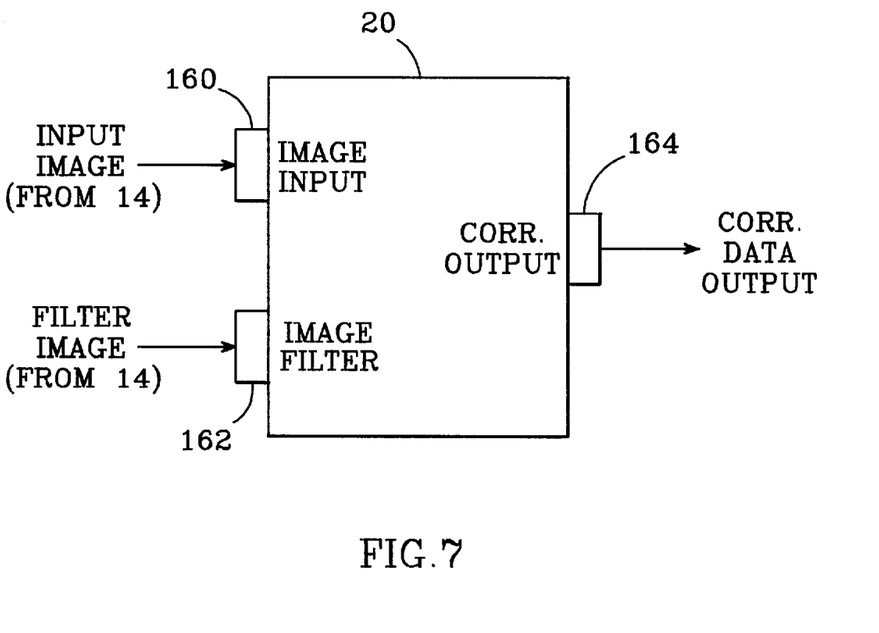
FIG. 7 is a symbolic diagram of an optical correlator used in the invention.

For purposes of describing the present invention, the optical correlator 20 may be considered functionally as an electro-optical device having three (electronic) ports, as shown in FIG. 7. The three ports include: (1) an image input port 160 for receiving an electronic signal encoding an input image for correlation; (2) a filter input port 162 for receiving a second electronic signal encoding a second image or "filter" for correlation; and (3) an output port 164, typically from a charge coupled device (CCD) imager, which converts the correlation image into electrical form for output. In addition the device requires a source (not shown) of preferably coherent electromagnetic radiation, typically a laser, which provides the medium used for computation.

Both the image input port 160 and the filter input port 162 are realized as two-dimensional spatial light modulators (SLMs) organized as two-dimensional image matrices, with addressable image pixels (typically arranged in the familiar row and column pattern). Accordingly, the input image must be formatted (suitably by image processor 14) to fit the matrix; and each pixel of data should preferably be addressed, under control of the image processor 14, to the spatially corresponding pixel on the SLM. For example, in one embodiment of the invention, the image input port and the filter input port are realized as 256×256 pixilated matrices. Accordingly, in this embodiment the image processor 14, as part of pre-processing steps 64 and 76 (in FIG. 4a), maps the ultrasonographic and the x-ray data onto a 256×256 matrix for output to the optical correlator 20. In a typical embodiment of the invention a Vanderlugt type optical correlator is used. In such a correlator the "filter" image must be pre-processed by two-dimensional Fourier transformation. In such an embodiment the image written to the filter port is preferably Fourier transformed by image processor 14 (for example in pre-processing step 76), to provide a frequency domain pattern. In an alternate embodiment, a joint transform correlator may be used as optical correlator 20. This eliminates the need for the digital Fourier transformation of the filter image, as the transformation is optically performed by the joint transform correlator.

When the input the filter images have been written to the input and filter ports 160 and 162, the optical correlator produces an output image which is a two dimensional output correlation pattern having an optical peak or peaks (bright spot) at the position of greatest correlation between the collapsed sonographic image and the radiographic image. The degree of correlation is indicated by the intensity of the output signal. The position of the output peak on the two-dimensional matrix of the correlator output CCD indicates the translations or shifts of the images relative to one another. The output image is read from the output photodetector (CCD) 164 by the image processor 14 in the conventional manner, typically by shifting the CCD voltage values out sequentially in rows (or columns) and then digitizing the output levels.

Although the invention is described in terms of linear transformations of the coordinates, such as translation, rotation, and scale multiplication, the invention is not limited to linear transformations. Non-linear transformations of coordinate systems may be useful in some applications. For example, the ultrasonographic information may be obtained with the breast differently deformed, as by a change of position of the subject, or by instrument pressure. By applying a mathematical transformation, which may in general be non-linear, a better mapping of the deformed subject breast onto the original subject breast can be obtained. Similarly, some scanning techniques may involve curvilinear, non-cartesian coordinate systems which would be treated with non-linear transformations.

While illustrative embodiments of the invention are described above, it will be evident to one skilled in the art that numerous variations, modifications and additional embodiments may be made without departing from the invention. For example, the construction of the ultrasound imaging system, the geometries and coordinate systems employed, or the type of radiographic image (including the radiographic medium) may be varied. The invention may be applied to multiple or stereo tactic radiographic images to correlate them to an independent source of ultrasonographic imagery. Computer aided tomographic (CAT) images, or even magnetic resonance images (MRI) may be correlated with ultra-sonographic imagery. Various means of data storage, transmission, or processing may be employed. The resolution or type of image that is sent from the image processor to the optical correlator could also be altered. Accordingly, it is intended that the invention be limited only in terms of the appended claims.

We claim:

1. An imaging method for modeling interior structures in a subject body, comprising the steps of:

providing radiographic and ultrasonographic images of an interior structure in different coordinate systems, and transforming the images to a common coordinate system to align the images with one another by (a) performing successive iterations of a coordinate transformation on one of the images in one of the different coordinate systems, (b) cross-correlating the images for each iteration, and (c) selecting a transformation which produces a selected degree of cross-correlation.

2. The imaging method of claim 1, wherein the selected degree of cross-correlation is the highest degree of cross-correlation among the cross-correlations obtained from said step of cross correlating the image for each iteration.

3. The imaging method of claim 1, wherein the step of cross-correlating is performed by an optical correlator.

4. The imaging method of claim 3, wherein the coordinate transformation comprises the step of rotating the one coordinate system.

5. The imaging method of claim 4, further comprising the steps of:
- analyzing one of the cross-correlations of the images to determine a positional offset of a correlation peak from an aligned correlation position, and
- translating one of the images to compensate for the positional offset.

6. The imaging method of claim 3, wherein the coordinate transformation comprises a change of scale.

7. The imaging method of claim 6, further comprising the steps of:
- analyzing a cross-correlation of the images to determine a positional offset of a correlation peak from an aligned correlation position, and
- translating one of the images to compensate for the positional offset.

8. The imaging method of claim 3, further comprising the steps of:
- deriving a slice from the ultrasonographic image which represents one or more layers of the ultrasonographic image, and
- cross-correlating the slice with at least a portion of the radiographic image.

9. The imaging method of claim 8, wherein the slice is derived from one or more image planes from the ultrasonographic image.

10. A method of locating the position of a structure shown in a three-dimensional region, comprising the steps of:
- providing radiographic and three-dimensional ultrasonographic imagery of the region including the structure,
- deriving a slice from the three-dimensional ultrasonographic imagery, the slice representing one or more layers of ultrasonographic imagery having a known associated position,
- cross-correlating the slice with at least a portion of the radiographic image, to produce an associated cross-correlation result, said cross-correlating step performed by an optical correlator,
- repeating the deriving and cross-correlating steps for multiple slices representing respective layers of ultrasonographic imagery lying at different respective positions within the three-dimensional ultrasonographic imagery, and
- comparing the respective cross-correlation results for the multiple slices to identify a slice which yields a selected degree of correlation in its associated cross-correlation result.

11. The method of claim 10 wherein the selected degree of correlation is the highest degree of correlation among the cross-correlation results associated with the multiple slices.

12. An apparatus for relating a radiographic image of a subject body to an ultrasonographic image, derived from a three-dimensional ultrasonographic data set representative of the subject body, comprising:
- an image processor programmed to store the ultrasonographic and radiographic images; and
- an optical correlator coupled to the image processor and arranged to correlate at least a portion of the stored ultrasonographic image with at least a portion of the stored radiographic image, and to produce an output which is indicative of the correlation between the correlated radiographic and ultrasonographic images.

13. The apparatus of claim 12, wherein the image processor is programmed to relate either the radiographic image or the ultrasonographic image to a spatial coordinate system, and to transform at least a portion of the other of the images to the spatial coordinate system.

14. The apparatus of claim 13, wherein the image processor is programmed to perform the transform so as to align the ultrasonographic and radiographic images in the spatial coordinate system.

15. The apparatus of claim 14 wherein the image processor is programmed to perform the transform as a linear transformation.

16. The apparatus of claim 15 wherein the image processor is programmed to perform the transform as at least one of:
(a) rotation;
(b)) translation; and
(c) scaling of the transformed image.

17. The apparatus of claim 14, wherein the image processor is further programmed to seek a transform which maximizes the correlation between the radiographic and ultrasonographic images.

18. A system for relating a radiographic image to an ultrasonographic image for displaying the internal structure of a subject body, comprising:
- an ultrasonic imaging system which produces an ultrasonographic image corresponding to the internal structures of the subject body;
- an image processor programmed to store at least a portion of the ultrasonographic and radiographic images; and
- an optical correlator coupled to the image processor and arranged to correlate at least a portion of the ultrasonographic image with at least a portion of the radiographic image, and to produce an output which is indicative of the correlation between the correlated radiographic and ultrasonographic images.

19. The system of claim 18, further comprising:
- a visual display coupled to the image processor to display information relating the ultrasonographic and radiographic images.

20. The system of claim 19, further comprising:
- a digitizing system arranged to digitize a radiographic image of the subject body, and to provide the radiographic image to the image processor in digital form.

21. The system of claim 20, further comprising:
- an x-ray imaging system arranged to provide the radiographic image of the subject body.

22. An image processing system comprising:
- input paths for a radiographic image and a three-dimensional volume ultrasonographic data set,
- an image processor, arranged to receive said radiographic image and three-dimensional volume ultrasonographic data set from said input paths and to construct a plurality of two-dimensional ultrasonographic images based on subsets of said ultrasonographic data sets,
- an optical correlator coupled to said image processor and arranged to correlate said radiographic image with each of said two-dimensional ultrasonographic images and to produce outputs representing the correlations associated with respective two-dimensional ultrasonographic images, for determining two-dimensional ultrasonographic images producing a selected degree of correlation with the radiographic image.

* * * * *